United States Patent
Bryant et al.

[11] Patent Number: 6,096,764
[45] Date of Patent: Aug. 1, 2000

[54] METHODS FOR INHIBITING DETRIMENTAL SIDE-EFFECTS DUE TO GNRH OF GNRH AGONIST ADMINISTRATION

[75] Inventors: Henry Uhlman Bryant, Indianapolis; George Joseph Cullinan, Trafalgar; Jeffrey Alan Dodge, Indianapolis, all of Ind.

[73] Assignee: Eli Lilly and Company, Indianapolis, Ind.

[21] Appl. No.: 09/134,316

[22] Filed: Aug. 14, 1998

Related U.S. Application Data

[60] Provisional application No. 60/056,202, Aug. 21, 1997.
[51] Int. Cl.[7] .................... A61K 31/445; A61K 31/40; A61K 31/38
[52] U.S. Cl. ................. 514/324; 514/422; 514/443
[58] Field of Search .................. 514/324, 422, 514/443

[56] References Cited

FOREIGN PATENT DOCUMENTS

| 738725 | 10/1996 | European Pat. Off. . |
| 747054 | 12/1996 | European Pat. Off. . |
| 747056 | 12/1996 | European Pat. Off. . |
| WO 97/27863 | 8/1997 | WIPO . |

OTHER PUBLICATIONS

Evans, et al, *Endocrinology*, 137(10):4139–4144 (1996).
Black, et al, *J. Clin. Ivest.*, 93(1):63–69 (1994).
Lips, et al, Nederlands Tijischrift Voor GeneeSkunde, 140(23):1215–1217 (1996).
Kauffman, et al, *J. Pharma. Exp. Ther.*, 280 (1):146–153 (1997).
Wang, et al., *Eur. J. Exp. Musculoskeletal Res.*, 4(3–4):171–175 (1995).
Frolik, et al., *Bone*, 18(6):621–627 (1996).
CA 109:86521, Ortmann et al., 1988.
CA 124:155994, Draper, Sep. 1995.

*Primary Examiner*—Kimberly Jordan
*Attorney, Agent, or Firm*—Gilbert T. Voy; James J. Sales

[57] ABSTRACT

A method of inhibiting detrimental side-effects of GnRH or GnRH agonist administration in a mammal which comprises the administration to a mannal in need thereof of an effective amount of a compound of formula I

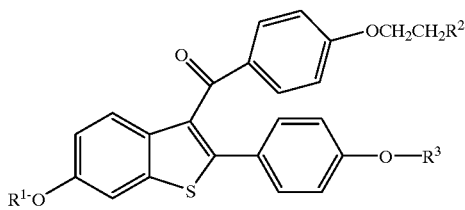

wherein $R^1$ and $R^3$ are, independently, —H, —$CH_3$, —CO($C_1$–$C_6$ alkyl), or —COAr, where Ar is optionally substituted phenyl;

$R^3$ is selected from the group consisting of pyrrolidine, piperidine, and hexamethyleneimino; or a pharmaceutically acceptable salt or solvate thereof.

12 Claims, No Drawings

METHODS FOR INHIBITING DETRIMENTAL SIDE-EFFECTS DUE TO GNRH OF GNRH AGONIST ADMINISTRATION

This Application claims the benefit of U.S. Provisional Application No. 60/056,202, filed Aug. 21, 1997.

FIELD OF THE INVENTION

The current invention relates to the areas of medicinal chemistry, pharmacology, and clinical medicine and methods of minimizing the detrimental side-effects caused by the utilization of GnRH or GnRH agonists.

BACKGROUND OF THE INVENTION

Gonadotropin-Releasing Hormone (GnRH), often referred to as Luteinizing Hormone Releasing Hormone (LHRH), is a ten amino acid peptide, produced and secreted by the hypothalamus. This peptide is conserved in all mammals and functions in similar fashion in both males and females. The major pharmacologic role of GnRH is to control the pituitary-gondanal axis. GnRH binds to specific receptors on pituitary cells and causes the release of gonadotropins. Subsequently, the gonadotropins exert their pharmacologic activity on the gonads controlling gametogensis and regulating the production of the sex steroids (estrogens, testosterones, and progestins).

Under normal physiological conditions, the hypothalamus produces GnRH in rhythmic pulses. However, if GnRH is present at a constant high level for an extended period of time, the cells of the pituitary become desensitized and cease producing gonadotrophins. Consequently, the cessation of gonadotrophin release causes the cessation of gametogenis and the production of the sex steroids. Thus, the constant presence of GnRH effects not only the reproductive potential, but other any other biological activities linked to the action of the sex steroids. In effect, high and constant levels of GnRH produce effects similar to those seen in female menopause or male castration.

The physiologic effects of menopause in women or castration in men are quite similar, e.g., hot flashes, weight gain, loss of libido, cardiovascular degeneration, osteoporosis, etc. Cardiovascular degeneration and osteoporosis are the two most potentially serious conditions induced by the continuous presence of GnRH. (For further information, see: "Goodman and Gilman's The Pharmacological Basis Of Therapeutics", Eds. Gilman, A. G., Rall, T. W., Nies, A. S., and Taylor, P., 8th Ed., Pergamon Press, NYC, Chap. 56, pp. 1352–1354 (1990)).

There are a variety of pathological conditions for which the continuous administration of GnRH or GnRH agonists have been of benefit. As mentioned supra, GnRH administration causes the cessation of sex steroid production which can be beneficial. For example, in women, the reduction of estrogen levels is very beneficial in the treatment of endometriosis, uterine fibroids, dysfunctional uterine bleeding, and the like; in men, the reduction of testosterone levels is very beneficial in the treatment of prostatic carcinoma, benign prostatic hypertrophy, and the like.

Despite the beneficial effects of continous GnRH, chronic administration can not be safely pursued due the detrimental side-effects, especially osteoporosis and hyperlipidemia (e.g., see: Synarel™ (Nafarelin Acetate) in "Physician's Desk Reference", Ed. 47, Medical Economics Co. Inc., Montvale N.J., pp. 2407–2408 (1993)). In general, continous GnRH or GnRH agonists are not used for periods greater than six months. Additionally, there are some potential uses for GnRH, such as birth control (male or female), which are not even able to be studied for extended periods of time due of the side-effect profile.

Although, all the detrimental side-effects of continous GnRH can be reversed by addition of estrogen or testosterone, their addition obviates the beneficial effects attempting to be achieved.

Clearly, it would of great utility to eliminate the detrimental side-effects associated with the continuous and chronic use of GnRH or GnRH agonists with a safe and non-countraproductive agent.

SUMMARY OF THE INVENTION

The current invention provides methods for inhibiting the detrimental side-effects associated with GnRH or GnRH agonist administration, in a mammal, which comprises the administration to a mammal in need thereof an effective amount of a compound of formula I

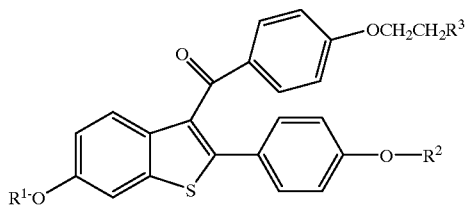

wherein $R^1$ and $R^3$ are, independently, —H, —$CH_3$, —CO($C_1$–$C_6$ alkyl), or —COAr, where Ar is optionally substituted phenyl;

$R^3$ is selected from the group consisting of pyrrolidine, piperidine, and hexamethyleneimino; or a pharmaceutically acceptable salt or solvate thereof.

DETAILED DESCRIPTION OF THE INVENTION

The current invention is related to the discovery that a select group of 2-aryl benzo [b]thiophenes (the compounds of formula I) are useful for the inhibiting detrimental side-effects associated with the continuous and chronic administration of GnRH or a GnRH agonist.

General terms used in the description of compounds herein described bear their usual meanings. For example, "$C_1$–$C_6$ alkyl" refers to straight or branched aliphatic chains of 1 to 6 carbon atoms including methyl, ethyl, propyl, iso-propyl, n-butyl, pentyl, hexyl and the like.

The term "substituted phenyl" refers to a phenyl group alone or having one or more substituents selected from the group consisting of $C_1$–$C_4$ alkyl, $C_1$–$C_4$ alkoxy, hydroxy, nitro, chloro, fluoro, or tri(chloro or fluoro)methyl. "O$C_1$–$C_4$ alkyl" refers a $C_1$–$C_4$ alkyl group attached through an oxygen bridge such as, methoxy, ethoxy, n-propoxy, iso-propoxy, and the like.

The term, "pharmaceutically accepted salt" refers to either acid or base addition salts which are known to be non-toxic and are commonly used in the pharmaceutical literature. Commonly used acid addition salts are inorganic salts formed by the addition of sulfuric acid, nitric acid, hydrochloric acid, hydrobromic acid phosphoric acid, phosphorous acid and the like; or organic salts formed by the addition of acetic acid, formic acid, benzoic acid, citric acid, methanesulfonic acid and the like. Commonly used basic addition salts are the salts formed by alkali or alkaline earth hydroxides, ammonium hydroxide, alkyl or aromatic amines and the like. A preferred salt of this invention is the hydrochloride salt.

The term "solvate" refers to a molecular complex of a compound of formula I with one or more solvent molecules. Such solvent molecules would be those commonly used in the pharmaceutical literature, which are known to be innocuous to the recipient, e.g., water, ethanol, and the like.

The term "inhibiting" is defined to include its generally accepted meaning which includes stopping, slowing or ameliorating. As such, the present invention encompasses both prophylactic and treatment therapies.

The compounds of this invention are derivatives of centrally located carbon, i.e., the "—CO—" moiety in formula I, thus derivatives are methanones, e.g., a compound of A—CO—B, would be named [A] [B]methanone. Further the compounds of formula I are derivatives of benzo[b]thiophene which is named and numbered according to the Ring Index, The American Chemical Society, as follows:

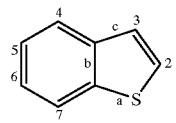

Thus, Raloxifene hydrochloride, which is a preferred embodiment of this invention, is a compound of formula I, where $R^1$ and $R^3$ are hydrogen and $R^2$ is a piperdinyl ring, the hydrochloride salt thereof. Raloxifene hydrochloride is named: [2-(4-hydroxyphenyl)-6-hydroxybenzo[b]thie-3-yl][4-[2-(1-piperidenyl)ethoxy]phenyl]methanone hydrochloride.

All of the compounds used in the methods and formulations of the current invention can be made according to procedures, such as those detailed in U.S. Pat. No. 4,133,814 and U.S. Pat. No. 4,418,068, each of which is included by reference, herein. In general, the process starts with a benzo[b]thiophene having a 6-hydroxyl group and a 2-(4-hydroxylphenyl) group. The starting compound is protected, alkylated, and de-protected to form the compounds of formula I. The formula I compounds which are carboxylic esters may be prepared by methods described in U.S. Pat. No. 5,393,763, which included by reference, herein.

The compounds of formula I have shown to have the potential for treating endometriosis (U.S. Pat. No. 5,461,065), uterine fibroids (U.S. Pat. No. 5,457,116), female fertility (U.S. Pat. No. 5,462,949), dysfunctional uterine bleeding (U.S. Pat. No. 5,460,153), intra al.

The general structure of GnRH and GnRH agonists is depicted in formula II, below:

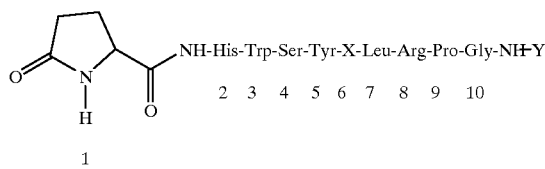

Where all the appropriate amino acids are as their natural L-configuration, except as noted below and pharmaceutically acceptable salts and solvates thereof.

Compounds within the scope of the current invention include, but are not limited to:

1) Native GnRH (Gonadorelin)(Lurepulse™); wherein X is Gly, Y is hydrogen, and as its acetate salt.
2) Leuprolide (Lupron™); wherein X is D-leucine, Y is —$CH_2CH_3$, and as its acetate salt (U.S. Pat. Nos. 4,005,063, 4,005,194, 4,652,441, 4,677,191, 4,728,721, and 4,849,228)
3) Histrelin (Supprelin™); wherein X is D-(N-benzyl)-His, Y is —$CH_2CH_3$, and as its acetate salt (U.S. Pat. No. 4,224,946)
4) Nafarelin (Synarel™); wherein X is D-3-(2-naphthyl)-Ala, Y is hydrogen, and as its acetate salt (U.S. Pat. No. 4,244,946)
5) Triptorelin; wherein X is D-Typ and Y is hydrogen.
6) Buserelin; wherein X is D-(O-t-butyl)Ser and Y is —$CH_2CH_3$.
7) Goserelin (Zoladex™); wherein X is O-(t-butyl)-serine, the tenth amino acid of formula II is replaced with azgly-$NH_2$, and as its acetate salt.

Such compounds are either commercially available, described in the references, supra, or can be readily prepared by ordinary methods in the art of peptide synthesis.

As used herein, the term "effective amount" means an amount of compound of formula I of the present invention which is capable of inhibiting detrimental side-effects, particularly osteoporosis or hyperlipidemia, due to GnRH orGnRH agonist administration.

By "pharmaceutically acceptable formulation" it is meant that the carrier, diluent, solvent, excipients and salt must be compatible with the active ingredient (a compound of formula I) of the formulation, and not be deleterious to the recipient thereof.

The term, "continuous therapy" used in describing the utilization of GnRH or a GnRH agonist, means a dose level and dose regimen of the GnRH agonists which causes a desensitization of the pituitary to GnRH, thus causing a cessation of gonadal function. This should be distinguished from those utilities in which GnRH or a GnRH agonist is administered in a pulsatile regimen. Such pulsatile methods are not preferred for the current invention.

The term, "chronic therapy" used in describing the utilization of GnRH or a GnRH agonist, means the administration of GnRH or a GnRH agonist for a period of time which causes detrimental side-effects to become apparent, e.g., bone loss, hyperlipidemia, intra al. The amount of time in which such side-effects manifest themselves may vary from patient to patient; however, a period of time longer than six months would be a likely criterium.

Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate and solid polyethyl glycols. Final pharmaceutical forms may be pills, tablets, powders, lozenges, syrups, aerosols, saches, cachets, elixirs, suspensions, emulsions, ointments, suppositories, sterile injectable solutions, or sterile packaged powders, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

In addition to formulations which are amenable to oral or parenteral use, compounds of the current invention may be prepared for continuous delivery. Such formulations would include, but not be limited to: an injectable, depo form or a subcutaneous implant.

Methods for the preparation of depo or implant formulation are known in the art. These methods would include, but not be limited to: the use of micro-encapsulation (microspheres) of the active moieties using bio-degradable polymers such as lipids (liposomes), copolymers of amino acids and sugars, and the like; suspensions which slowly degrade which would be homogeneous mixtures of the active moieties with agents such as oils or lipids; formulations of the active moieties coated on the surface of non-degradable substraits (implants); and the like. Incorporated amounts of compounds of formula I, as well as, the composition of the sustained-release formulation may be varied depending on the particular pathologogies being treated and the desired length of time for the delivery of the moieties. In general, desirable lengths of time for drug released for such sustained release formulations may be one week to a year; however more usual would be several weeks to several months.

The particular dosage of a compound of formula I required to inhibit the detrimental side-effects of GnRH or GnRH administration according to this invention will depend upon the particular symptoms and severity. Such considerations as a dosage, route of administration, and frequency of dosing are best decided by the attending physician. Generally, accepted and effective doses for oral or parenteral administration will be from 10 mg to 800 mg, and more typically between 20 mg and 100 mg. A particularly preferred dose is 60 mg/day via the oral route, especially in a post-menopausal female. Such dosages will be administered to a patient in need of treatment from once to three times each day or as often as needed to effectively control inhibit the side-effects.

The formulations which follow are given for purposes of illustration and are not intended to be limiting in any way. The total active ingredients in such formulations comprises from 0.1% to 99.9% by weight of the formulation. The term, "active ingredient" means a compound of formula I, preferably Raloxifene hydrochloride.

| Formulation 1: Gelatin Capsules | |
|---|---|
| Ingredient | Quantity (mg/capsule) |
| Active Ingredient | 50–600 |
| Starch NF | 0–500 |
| Starch flowable powder | 0–500 |
| Silicone fluid 350 centistrokes | 0–15 |

The ingredients are blended, passed through a No. 45 mesh U.S. sieve, and filled into hard gelatin capsules.

| Formulation 2: Tablets | |
|---|---|
| Ingredient | Quantity (mg/tablet) |
| Active Ingredient | 50–600 |
| Starch | 10–50 |
| Cellulose, microcrystalline | 10–20 |
| Polyvinylpyrrolidone (as 10% solution in water) | 5 |
| Sodium carboxymethyl cellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethyl cellulose, magnesium stearate, and talc, previously passed through a No. 60 mesh U.S. sieve, are added to the above granules and thoroughly mixed. The resultant material is compressed in a tablet forming machine to yield the tablets.

| Formulation 3: Aerosol | |
|---|---|
| Ingredient | Weight % |
| Active Ingredient | 0.50 |
| Ethanol | 29.50 |
| Propellant 22 (Chlorodifluoromethane) | 70.00 |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

| Formulation 4: Suspension Suspensions each containing 100 mg of a compound of formula I per 5 mL dose. | |
|---|---|
| Ingredient | Weight |
| Active Ingredient | 100 mg |
| Sodium carboxymethyl cellulose | 50 mg |
| Syrup | 1.25 mL |
| Benzoic acid solution (0.1M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the entire mixture to the required volume.

| Formulation 5 Depo Suspension | |
| --- | --- |
| Active Ingredient | 50–500 mg |
| Purified Gelatin | 100–800 mg |
| Lactic acid-glycolic acid coploymer | 100–1000 mg |
| Lactose | 10–50 mg |

The active ingredient is dissolved in water and the copolymer is added and mixed. The water is removed by evalaporation and the product milled to the desired size. The resulting microsheres are mixed with the remaining ingredients to form a homogeneous mixture which is amplued. The microspheres are reconstituted, for use, in a suspending diluent, such as water containing ehancing agents such as mannitol, carboxymethylcellulose, and the like.

GnRH and GnRH agonist, being peptides, are not well absorbed or stable to oral administration, thus parenteral administration is necessary. Pharmaceutical formulations for the GnRH or a GnRH agonist should be amenable to the continous release or continuous pharmaceutical action. Many formulations and methods for GnRH or a GnRH agonist, found in the art, are designed for the pulsatile action of these hormones. Although, pulsatile action is appropriate for certain applications and are necessary to avoid dilaterious side-effects; such formulations and methods are not preferred for uses envisioned in the current invention.

The formulations and methods for GnRH and GnRH agonists that are would be preferred would include, but not be specifically limited to, administration which would be by daily injection, daily inhalation, or a continuous release form such as a depo, subcutaneous form. Such forms of GnRH and GnRH agonists are known in the art, c.f., "Physician's Desk Reference", 47th Ed., Medical Economics Co., Montvale N.J., 1993, pp.1134, 1716, 1937, 2407, 2420–2424.

The amount of GnRH or GnRH agonist administered to a patient would depend on the pathology being treated and particular agonist and formulation being used. These parameters are best determined by the attending physician. In general, 0.1 to 50 mg per day is sufficient and 0.5 to 5 mg more commonly used, when daily injections are used. If the GnRH agonist is used in a continuous release form, such as a depo-form, dosage amounts vary depending on the particular composition, (see: references cited, supra).

A convenient formulation for the methods of the current invention would comprise a compound of formula I and GnRH or a GnRH agonist in the same composition. For example, an aerosol formulation comprising Raloxifene HCl and Leuprolide acetate could be used. Such a formulation would be administered several times a day in order to maintain a high level of the GnRH agonist, critical for the methods of the current invention. Since constant, high levels of GnRH agonists are important to maintain, a very convenient formulation would comprise a compound of formula I and GnRH or a GnRH agonist in a injectable, depo form or a subcutaneous implant.

Methods for the preparation of depo or implant formulation are known in the art. These methods would include, but not be limited to: the use of micro-encapsulation (microspheres) of the active moieties using bio-degradable polymers such as lipids (liposomes), copolymers of amino acids and sugars, and the like; suspensions which slowly degrade which would be homogeneous mixtures of the active moieties with agents such as oils or lipids; formulations of the active moieties coated on the surface of non-degradable substraits (implants); and the like.

| Formulation 6 Depo Suspension | |
| --- | --- |
| Raloxifene hydrochloride | 50–500 mg |
| Leuprolide acetate | 2–10 mg |
| Purified Gelatin | 100–800 mg |
| Lactic acid-glycolic acid coploymer | 100–1000 mg |
| Lactose | 10–50 mg |

Raloxifene hydrochloride and leuprolide acetate are dissolved in water and the copolymer is added and mixed. The water is removed by evaporation and the product milled to the desired size. The resulting microspheres are mixed with the remaining ingredients to form a homogeneous mixture which is amplued. The microspheres are reconstituted, for use, in a suspending diluent, such as water containing enhancing agents such as mannitol, carboxymethylcellulose, and the like.

As a demonstration of the methods of the current invention, in particular the inhibition of bone loss due to the administration of GnRH agonists, the following experiment was performed in female rats.

Six month old, female, Sprague-Dawley rats were obtained from Charles River Laboratories (Portage Mich.). The animals were housed in cages with a 12 hr. dark-light cycle, kept at a temperature of 22° C., and food (0.5% calcium and 0.4% phosphorus) and water available, ad librium. The animals were acclimated to these conditions for two weeks and then randomized into six animal, test and control groups.

Test group and control animals were implanted with Alzet 2002 minipumps for continuous infusion. The minipumps were implanted under light isoflurane anesthesia via a small (1 cm) dorsal incision, which was closed with autoclips following subcutaneous implantation. The minipumps were set up to deliver 0.1% bovine serum albumin in sterile water for the pacebo control. The GnRH treatment groups and controls had minipumps set up to deliver 25 $\mu$g per day of [D-Trp$^6$] GnRH agonist(Bachem Biosciences, King of Prussia PA) in 0.1% bovine serum albumin in sterile water. Since the minipumps have a operational life time of approximately two weeks in vivo, the minipumps were replaced on days 14 and 28 of the following experiments. The test compounds (formula I) were dissolved in an aqueous solution of 20% $\beta$-hydroxycyclodextrin in a volume of 0.1 mL/kg of animal body weight and administered by oral gavage. Placebo and GnRH control groups received an aqueous solution of 20% $\beta$-hydroxycyclodextrin in a volume of 0.1 mL/kg of animal body weight and administered by oral gavage. The animals were dosed for thirty-five days, at the end of which the animals were anesthetized with carbon dioxide. Blood samples were obtained by cardiac puncture. The animals were euthanized by carbon dioxide asphyxiation and the left femora and tibiae were collected. Femora were frozen at −20° C. for later X-ray analysis and tibiae wre placed in 50% EtOH for densitometric analysis.

Bone Analysis

Computed tomography was conducted with a 960 pQCT (Norland/Stratec, Ft. Atkinson Wis.) to scan the first 1.2 mm region of the left proximal tibia below the proximal separation point between the fibula and tibial. Cross-sectional area and mineral content (hydoxyapatite in mg) and bone mineral density (hydroxyapatite concentration in mg/cc)

were calculated using Dichte (Stratec) software version 5.1. Voxel dimensions of 0.149×0.149×1.2 mm were used.

The distal end of the left femur was scanned on a Nicholet NXR-1200 real-time X-ray imaging system (Madison, Wis.). The digitalized X-ray images generated with this system were captured using the NIH image (1.45) software package and gray levels were analyzed using the Ultimage software package (Graftek, Meudon-la-Foret, France). Briefly, a standardized region of interest (2.6×5.6 mm) was placed just proximal to the growth plate region of the femur distal metaphysis, and centered in the shaft of the bone. The average gray scale was computed for this region over the pixel intensity range of 0 to 40. Then relative comparisons were made with resept to the [D-Trp$^6$]-GnRH controls.

Serum Cholesterol Analysis

Blood samples were allowed to clot at 4° C. for two hours and then centrifuged at 2,000×g for 10 minutes. Serum cholesterol was determined using a Boehringer Mannheim Diagnostics (Indianapolis, Ind.) high performance cholesterol colorimetric assay.

Statistics

Statistical evaluations of the effects of the compounds of the current invention on the various parameters were made by one-way analysis of variance (ANOVA) with post-hoc Fisher's PLSD analysis.

TABLE 1

| Group | Femur Image Analysis (gray scale) | Tibia BMD (mg/cc) | Tibia BMC (mg) | Tibia Cross-area (mm$^2$) |
| --- | --- | --- | --- | --- |
| Placebo[a] | 55.0* | 675 | 13.7 | 20.3 |
| [D-Trp$^6$]GnRH | 31.3 | 652 | 12.8 | 19.6 |
| Raloxifene 0.1 mg/kg | 47.8 | 651 | 15.1 | 23.3* |
| Raloxifene 1.0 mg/kg | 51.8* | 732* | 15.3* | 20.9 |

[a]five animals in this group
*p < 0.05 vs the GnRH control

The results shown in Table 1 demonstrate the ability of the compounds of formula I to inhibit or protect the animals from bone loss induced by a GnRH agonist.

Another aspect of the detrimental side-effects that GnRH agonists exhibit is an increase in serum lipids due to a cessation of ovarian function (see: U.S. Pat. No. 5,464,845). The resultant lack of estrogen production causes serum cholesterol to rise in fashion similar to that seen in normal female menopause. The results shown in Table 2 demonstrate the utility of the compounds of formula I to lower serum cholesterol in GnRH agonist treated female rats.

TABLE 2

| Group | Serum Cholesterol (mg/dL) +/− SEM |
| --- | --- |
| Placebo[a] | 97 +/− 4 |
| [DTrp$^6$]GnRH | 106 +/− 10 |
| Raloxifene 0.1 mg/kg | 68 +/− 6* |
| Raloxifene 1.0 mg/kg | 60 +/− 8* |

[a]five animals in this group
*p < 0.05 vs the GnRH control

A common pathology, which is treated by GnRH agonists, is prostatic disease in men. Because GnRH functions in a similar manner in both sexes, administration of GnRH in men causes a condition in which the testes cease to function, i.e., a pharmacological induced orchiectomy. Loss of sex hormone production in men has a similar detrimental side-effect as seen in women, i.e., loss of bone (osteoporosis) (see: Seeman E. 1995. The dilemma of osteoporosis in men. Am. J. Med. 98(suppl. A): 2A76S-2A88S), hyperlipidemia, inter al. As an experimental demonstration of the utility of the compounds of the current invention (formula I) to inhibit or prevent the detrimental side-effects induced by the cessation of gonadal function in males, the following experiment was performed.

Six month old, sham-operated or orchiectomized(ORX), Sprague-Dawley rats were obtained from Charles River Laboratories (Portage Mich.). The animals were housed in cages with a 12 hr. dark-light cycle, kept at a temperature of 22° C., and food (0.5% calcium and 0.4% phosphorus) and water available, ad librium. The animals were shipped after surgery and upon delivery were randomized into six animal, test and control groups. The animals were acclimated to these conditions for three days. Animals were dosed with the test compound (Raloxifene) in the same manner as described, supra. Analysis of the bone parameters were the done in the same manner as described, supra. Although the data tended to have variation between the sham and orchiectomized, the data in Table 3 demonstrates the inhibition of bone loss with use of the compounds of formula I.

TABLE 3

| Group | Femur Image Analysis (gray scale) | Tibia BMD (mg/cc) | Tibia BMC (mg) | Tibia Cross-area (mm$^2$) |
| --- | --- | --- | --- | --- |
| Sham Control | 65* | 455 | 12.9* | 28.3* |
| ORX Control | 48 | 487 | 11.4 | 23.4 |
| Raloxifene | | | | |
| 0.1 mg/kg | 70* | 506 | 12.3 | 24.3 |
| 0.3 mg/kg | 64 | 527* | 12.8* | 24.4 |
| 1.0 mg/kg | 82* | 562* | 14.7* | 26.2* |
| 3.0 mg/kg | 73* | 557* | 13.7* | 24.5 |
| 10.0 mg/kg | 82* | 586* | 15.0* | 25.6* |

*p < 0.05 vs ORX control

From the data presented in Table 3, that males being treated with continuous and chronic GnRH or GnRH agonists should be protected from the induced bone loss. The current invention should be especially useful for males suffering from prostatic cancer or benign prostatic hypertrophy (BPH).

We claim:

1. A method of inhibiting GnRH or GnRH agonist induced detrimental side-effects due to administration of GnRH or a GnRH agonist to a mammal, comprising administrating to a mammal in need thereof an effective amount of a compound of formula I

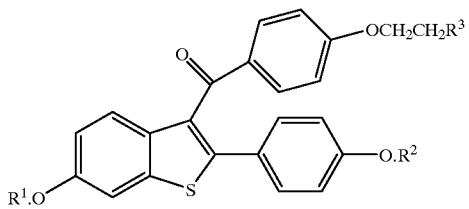

wherein R$^1$ and R$^2$ are, independently, —H, —CH$_3$, —CO(C$_1$–C$_6$ alkyl) or —COAr, where Ar is optionally substituted phenyl;

R$^3$ is selected from the group consisting of pyrrolidine, piperidine, and hexamethyleneimino; or a pharmaceutically acceptable salt or solvate thereof.

2. A method according to claim 1 wherein said compound is [2-(4-hydroxyphenyl)-6-hydroxybenzo[b]thien-3-yl][4-[2-(1-piperidinyl)ethoxy]phenyl]methanone hydrochloride.

3. A method of claim 1 wherein said mammal is a post-menopausal woman.

4. A method according to claim 3 wherein a compound of formula I is administered in an amount of 60 mg/day via the oral route.

5. The method according to claim 1 wherein the GnRH agonist is a compound selected from leuprolide acetate, histrelin acetate, nafarelin acetate, triptorelin acetate, buserelin acetate, goserelin acetate, or gonadorelin acetate.

6. The method according to claim 1 wherein said side-effect is bone loss.

7. The method according to claim 1 wherein said side-effect is hyperlipidemia.

8. A pharmaceutical formulation, comprising a compound of formula I of claim 1, and GnRH or a GnRH agonist, along with one or more pharmaceutically acceptable carriers, diluents, or excipients.

9. A pharmaceutical formulation according to claim 8 wherein said compound of formula I is Raloxifene hydrochloride.

10. A pharmaceutical formulation according to claim 9 wherein the GnRH agonist is a compound selected from leuprolide acetate, histrelin acetate, nafarelin acetate, triptorelin acetate, buserelin acetate, goserelin acetate, or gonadorelin acetate.

11. A pharmaceutical formulation according to claim 9 which is suitable for sustained release via a depo, subcutaneous formulation.

12. A pharmaceutical formulation according to claim 11 wherein said depo formulation is an implant device.

* * * * *